United States Patent
Ma

(10) Patent No.: US 6,695,363 B1
(45) Date of Patent: Feb. 24, 2004

(54) METHOD AND SYSTEM FOR SECONDARY LOCK FOR SECURING ACCESSORIES IN A RADIATION THERAPY SYSTEM

(75) Inventor: Edmund Leung Ma, Alameda, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 09/489,573

(22) Filed: Jan. 21, 2000

(51) Int. Cl.[7] ................................................ E05C 3/16
(52) U.S. Cl. ...................................... 292/227; 292/127
(58) Field of Search ........................... 292/227, 27, 110, 292/111, 113, 124, 127, 222, 224, 197; 600/227

(56) References Cited

U.S. PATENT DOCUMENTS

| | | | | |
|---|---|---|---|---|
| 362,936 A | * | 5/1887 | Chantrell | |
| 983,647 A | * | 2/1911 | Romines | |
| 2,955,859 A | * | 10/1960 | Krause | |
| 3,194,595 A | * | 7/1965 | Wheeler | 292/113 |
| 3,841,693 A | * | 10/1974 | Reynolds | 296/35 R |
| 3,891,254 A | * | 6/1975 | Lile | 292/113 |
| 3,918,750 A | * | 11/1975 | Okamoto | 292/106 |
| 4,053,177 A | * | 10/1977 | Stammereich | 292/113 |
| 4,159,153 A | * | 6/1979 | Yoshikawa | 312/333 |
| 4,720,611 A | * | 1/1988 | Ishii | 200/61.61 |
| 4,759,574 A | * | 7/1988 | James | 292/113 |
| 4,875,724 A | * | 10/1989 | Gruber | 292/216 |
| 5,785,362 A | * | 7/1998 | Nadherny | 292/98 |
| 6,523,867 B1 | * | 2/2003 | Yeh | 292/63 |

* cited by examiner

Primary Examiner—Gary Estremsky

(57) ABSTRACT

The present invention provides a method and system for a secondary lock for securing accessories in a radiation therapy system. The latching mechanism provided in accordance with the present invention includes a primary lock, a secondary lock, and a retainer shaft. The primary lock includes a head at a first end of the primary lock, and a protrusion at a first side of the primary lock. The secondary lock includes a main body, an engagement tang at a first end and a first side of the main body, and a locking tang at the first end and a second side of the main body. The retainer shaft is coupled to the primary lock and the main body of the secondary lock, where the secondary lock is fixedly positioned when the protrusion engages the accessory and the head resides between the engagement tang and the locking tang. The secondary lock creates a fail-safe locking system, such that the secondary lock causes the primary lock to continue to engage an accessory tray even if failure occurs elsewhere in the latching mechanism. This lowers the probability of failure of the latching mechanism significantly, resulting in a safer radiation therapy system. The secondary lock of the latching mechanism also remains in a disengaged position when no tray in inserted, allowing trays to be inserted without the need to press the release button first to set the secondary lock into the disengaged position.

8 Claims, 16 Drawing Sheets

Top View

Top View

Side View

Top View

Top View

Side View

Side View

Side View

METHOD AND SYSTEM FOR SECONDARY LOCK FOR SECURING ACCESSORIES IN A RADIATION THERAPY SYSTEM

FIELD OF THE INVENTION

The present invention relates to latching mechanisms, and more particularly to latching mechanisms for securing accessories in a radiation therapy system.

BACKGROUND OF THE INVENTION

Radiation therapy systems for the treatment of cancer are well known in the art. FIG. 1 illustrates one such system manufactured by Siemens Medical Systems, Inc.™. The system 10 includes a platform 20 onto which a cancer patient lies. The rotating gantry 30 administers the radiation to the patient. The rotating gantry 30 includes an accessory holder 100 onto which accessory trays (not shown) may be inserted. The trays help an operator aim the radiation beam onto the patient. For example, a tray may contain a block or a filter to vary the concentration of the radiation beam. The tray may also have a hole patterned to match the shape of a patient's tumor to help focus the radiation beam. The trays are made of metal, typically one to two inches thick.

FIGS. 2A and 2B illustrate a top view and a cross-sectional view, respectively, of an accessory holder for a conventional radiation therapy system. The accessory holder 100 is herein described with simultaneous reference to FIGS. 2A and 2B. The accessory holder 100 comprises a frame 102 which contains three slots 104, 106, 108 into which accessory trays, such as tray 110, may be inserted. The trays are latched to the frame 102 by latching mechanisms 112, 114, 116. Each of the latching mechanisms 112 and 114 comprises a lock 118. The lock 118 has a head 120 at one end and a protrusion 122 at the side of the lock 118 nearer the tray 110. A roll pin 124 couples the lock 118 to a release assembly 126. Coupled at the opposite end of the release assembly 126 is a release button 128 which when pressed, compresses a button spring 130.

The latching mechanisms 112 and 114 are coupled to the frame 102 by a retainer assembly 132 which includes a retainer shaft 134. When the tray 110 is inserted into the slot 104, the protrusion 122 of the lock 118 engages a notch 136 on the tray 110, preventing the tray 110 from sliding out of the slot 104. An opening 154 in the frame 102 allows the lock 118 to freely engage the notch 136. When the release button 128 is pressed, the release assembly 126 pivots the lock 118 counterclockwise about the retainer shaft 134, releasing the tray 110. This is facilitated by the wedging action between an elongated hole 152 of the release assembly 126 and the roll pin 124. The release button 128 is spring loaded. This button spring 130 keeps the lock 118 engaged when a tray is inserted. A crescent washer 138 is used to constrain the latching mechanisms 112 and 114 in the direction of the retainer shaft 134 axis. The compliance of the crescent washer 138 limits the friction in the latching mechanisms 112, 114 while maintaining precision. The spacer 140 maintains the proper height alignment between the latching mechanisms 112 and 114 and their respective slots 104 and 106. The latching mechanism 116 for slot 108 uses a retainer ring 142 to loosely constrain the parts. The release assembly 144, the roll pin 146, the lock 148, and the spacer 150 for latching mechanism 116 perform the same functions as those for latching mechanisms 112 and 114.

However, the dislodgment of the roll pin 124 and/or the loss of release button spring 130 force due to breakage of the spring 130 or loosening of the release button 128 have been known to occur. If one of these failures occur, then the tray 110 is in danger of sliding out of the accessory holder 100 and falling onto a patient on the platform 20, possibly causing serious injuries.

Accordingly, what is needed is a system and method for a secondary lock for securing accessories in a radiation therapy system. The secondary lock should decrease the possibility of a failure of the accessory holder's latching mechanism. The present invention addresses such a need.

SUMMARY OF THE INVENTION

The present invention provides a method and system for a secondary lock for securing accessories in a radiation therapy system. The latching mechanism provided in accordance with the present invention includes a primary lock, a secondary lock, and a retainer shaft. The primary lock includes a head at a first end of the primary lock, and a protrusion at a first side of the primary lock. The secondary lock includes a main body, an engagement tang at a first end and a first side of the main body, and a locking tang at the first end and a second side of the main body. The retainer shaft is coupled to the primary lock and the main body of the secondary lock, where the secondary lock is fixedly positioned when the protrusion engages the accessory and the head resides between the engagement tang and the locking tang. The secondary lock creates a fail-safe locking system, such that the secondary lock causes the primary lock to continue to engage an accessory tray even if failure occurs elsewhere in the latching mechanism. This lowers the probability of failure of the latching mechanism significantly, resulting in a safer radiation therapy system. The secondary lock of the latching mechanism also remains in a disengaged position when no tray in inserted, allowing trays to be inserted without the need to press the release button first to set the secondary lock into the disengaged position.

DETAILED DESCRIPTION

The present invention provides a system and method for a secondary lock for securing accessories in a radiation therapy system. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. Thus, the present invention is not intended to be limited to the embodiment shown but is to be accorded the widest scope consistent with the principles and features described herein.

The secondary lock provided in accordance with the system and method of the present invention creates a latching mechanism with a fail-safe locking system where the conditions are safe even if normal operation is lost. This fail-safe system is provided by the secondary lock which causes the primary lock to continue to engage an accessory tray even if failure occurs elsewhere in the latching mechanism. This lowers the probability of failure of the latching mechanism significantly, resulting in a safer radiation therapy system.

To more particularly describe the features of the present invention, please refer to FIGS. 3 through 15 in conjunction with the discussion below.

Figure 2B:
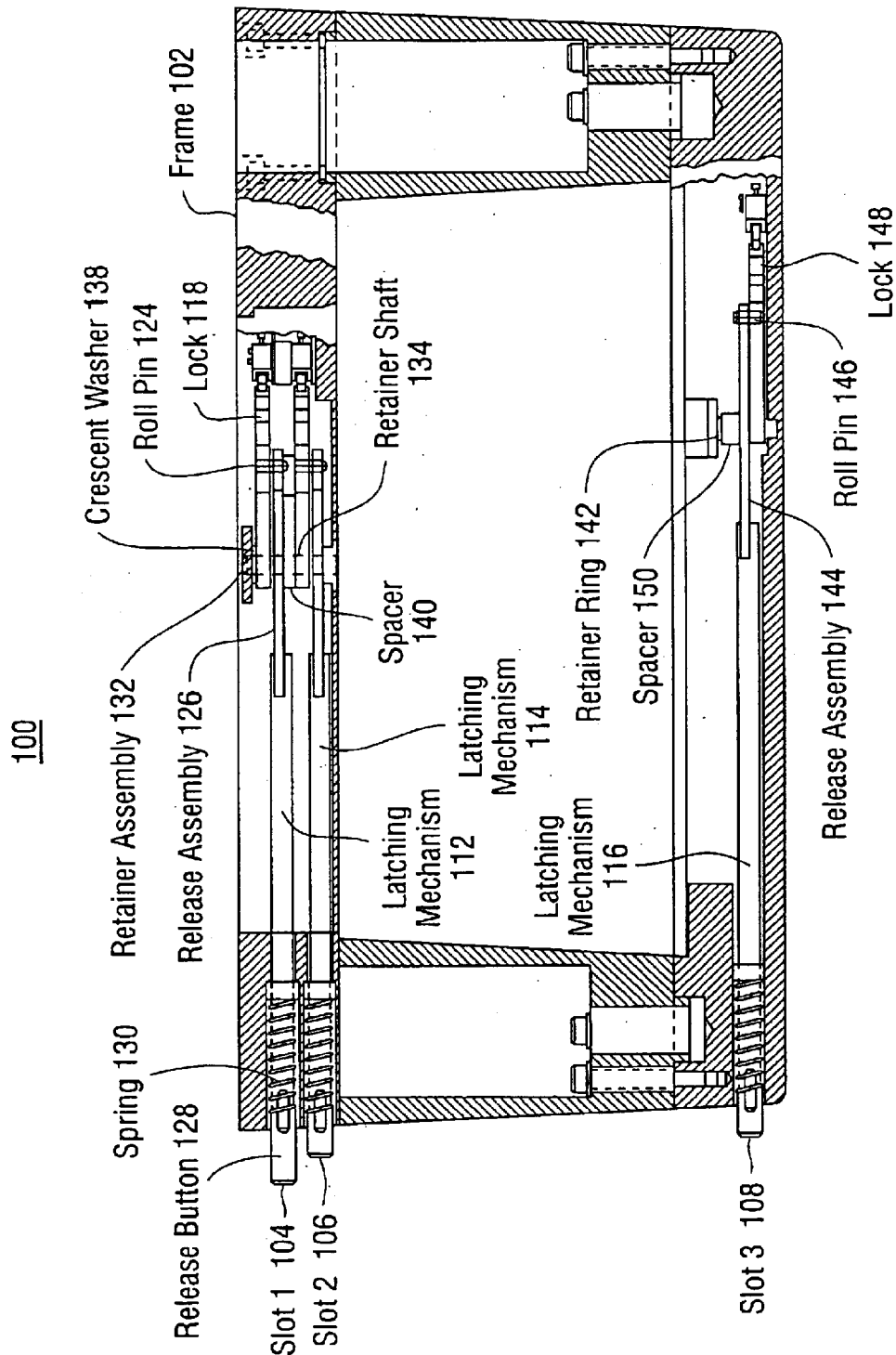
Figure 3:
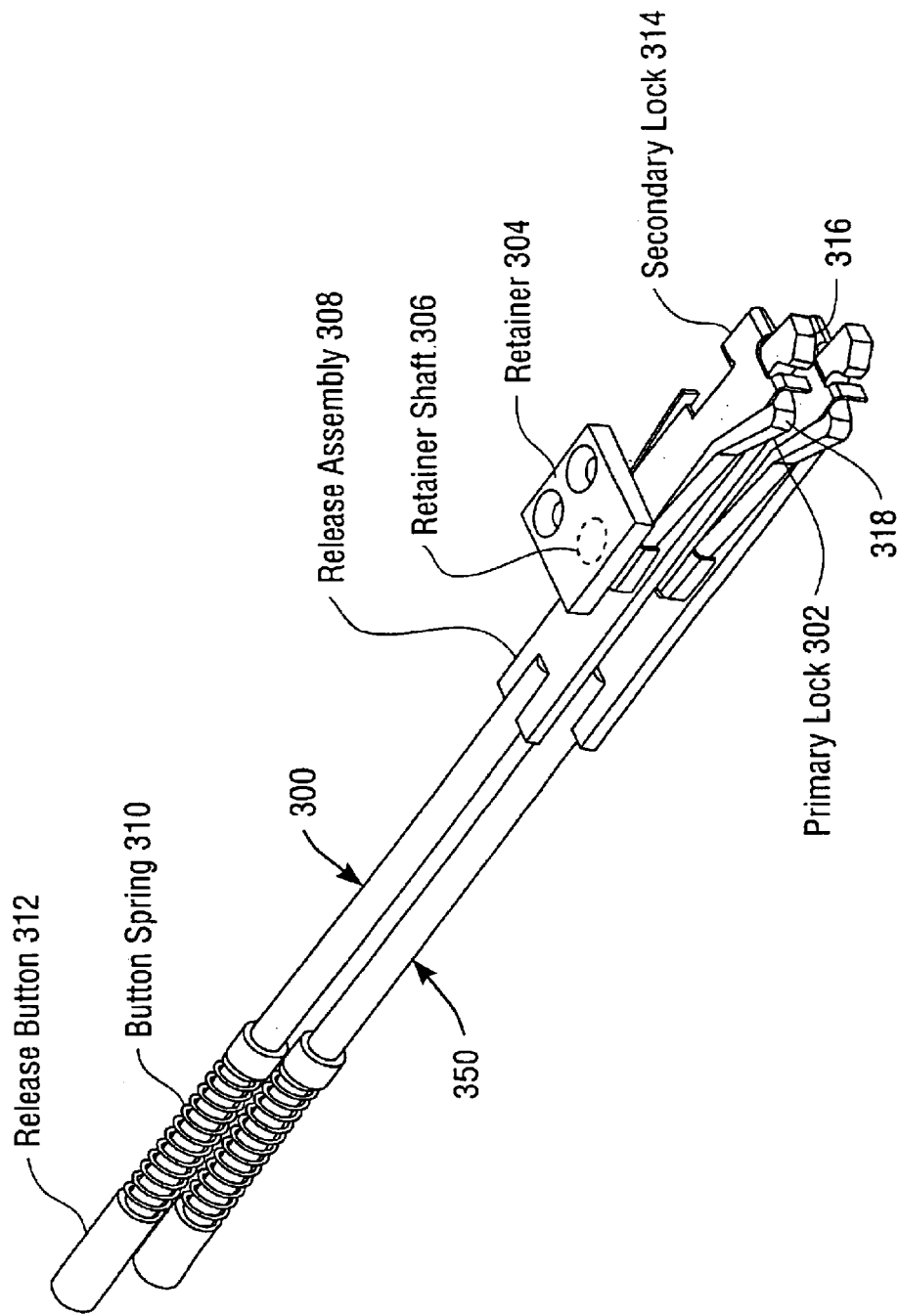
FIGS. 3 and 4 illustrate a preferred embodiment of a latching mechanism with a secondary lock in accordance with the present invention.
Figure 4:
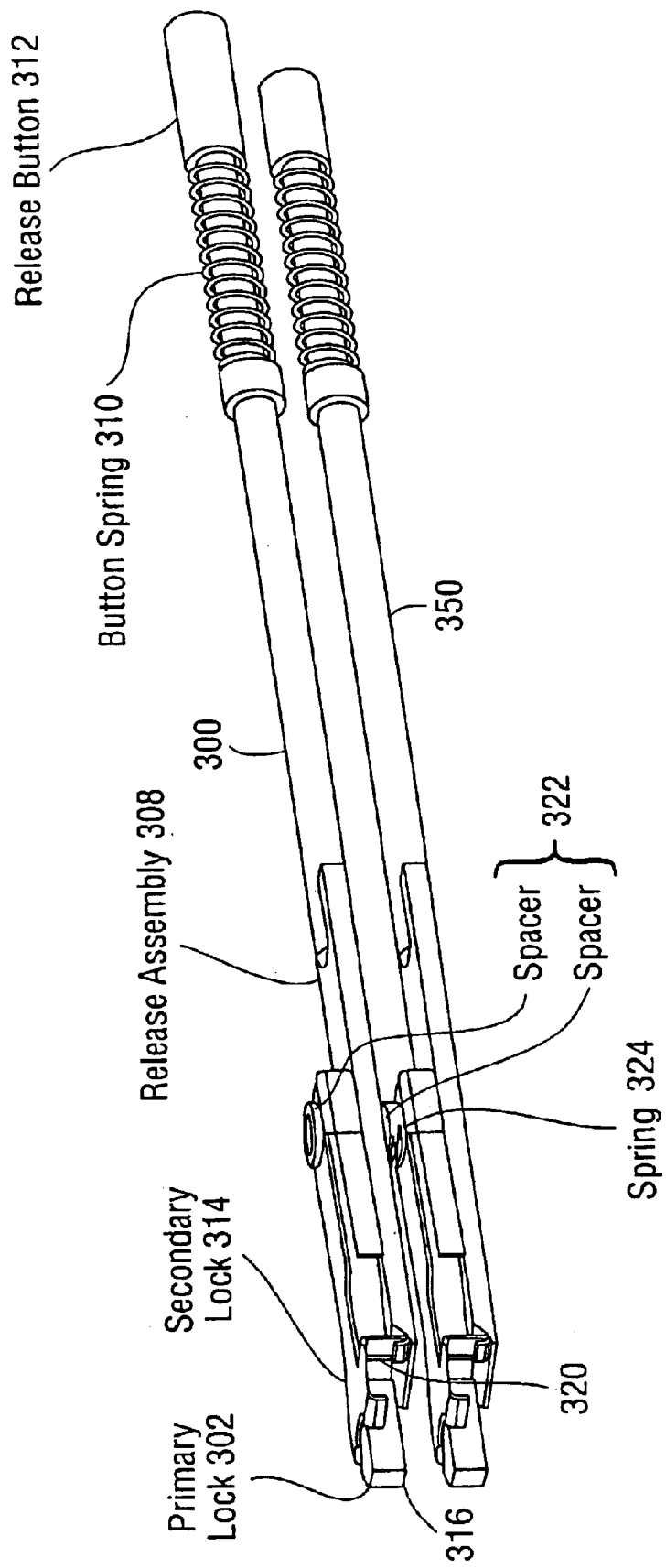

FIGS. 3 and 4 illustrate a preferred embodiment of a latching mechanism with a secondary lock in accordance with the present invention. FIGS. 3 and 4 illustrate the latching mechanisms 300 and 350 from two different angles. The latching mechanism 300 would latch an assembly tray in slot 104 of the assembly holder 100 (FIG. 2B) while latching mechanism 350 would latch an assembly tray in slot 106. The latching mechanisms 300 and 350 are described herein in reference to latching mechanism 300 and with simultaneous reference to FIGS. 3 and 4. Latching mechanism 350 has the same structure as latching mechanism 300.

Figure 1:
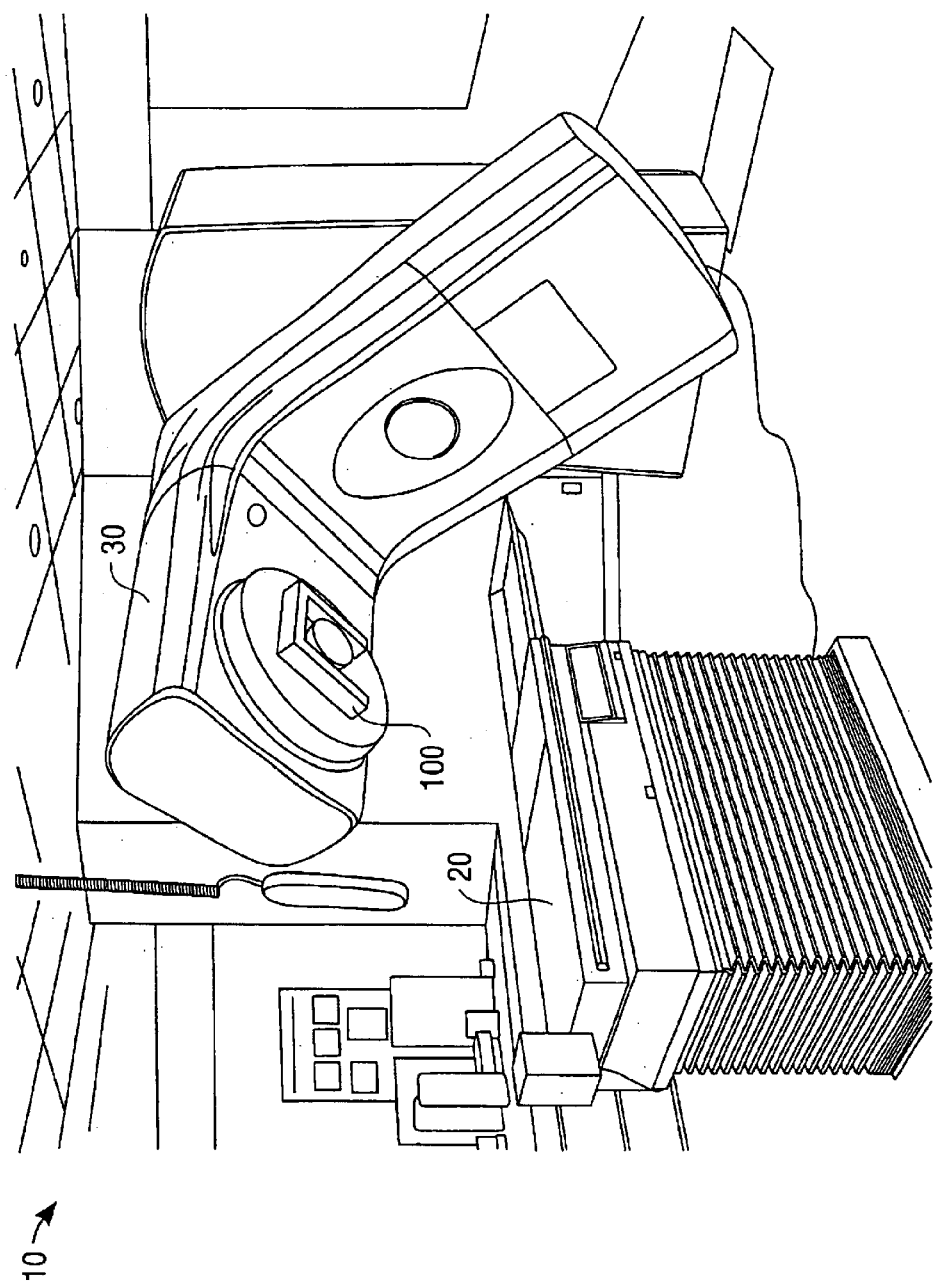
FIG. 1 illustrates a conventional radiation therapy system.
Figure 2A:
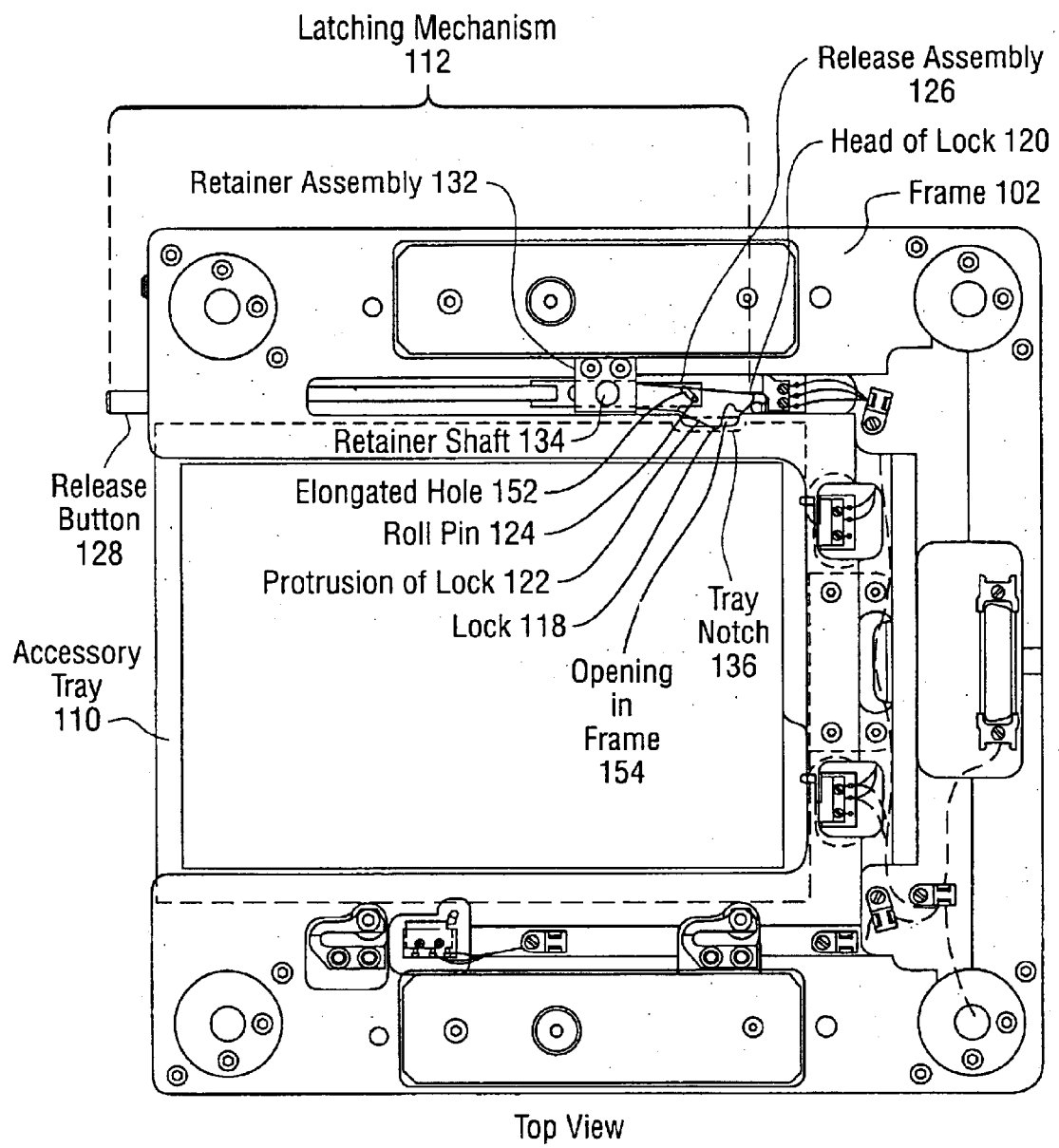
FIGS. 2A and 2B illustrate a top view and a cross-sectional view, respectively, of an accessory holder for a conventional radiation therapy system.

The latching mechanism 300 comprises a retainer assembly 304 with a retainer shaft 306, a release assembly 308, a button spring 310, and a release button 312. These elements perform the same functions as the retainer assembly 132, the retainer shaft 134, the release assembly 126, the button spring 130, and the release button 128, respectively, of the conventional latching mechanism 112 (FIGS. 2A and 2B). Like the conventional lock 118, the primary lock 302 of the latching mechanism 300 also comprises a head 316 and a protrusion 318 at the side nearer to the tray. But the primary lock 302 comprises an additional notch 320 at the side farther from the tray, as illustrated in FIG. 4. The latching mechanism 300 also further comprises a secondary lock 314, which ensures the functionality of the primary lock 302. The primary 302 and secondary 314 locks are able to pivot clockwise and counterclockwise around the retainer shift 306 axis. A self-clinching type pin (not shown) is coupled between the release assembly 308 and the primary lock 302 which performs the same function as the roll pin 124 of the conventional latching mechanism 112. As illustrated in FIG. 4, the latching mechanisms 300 and 350 are separated by spacers 322 and spring 324.

Figure 5:
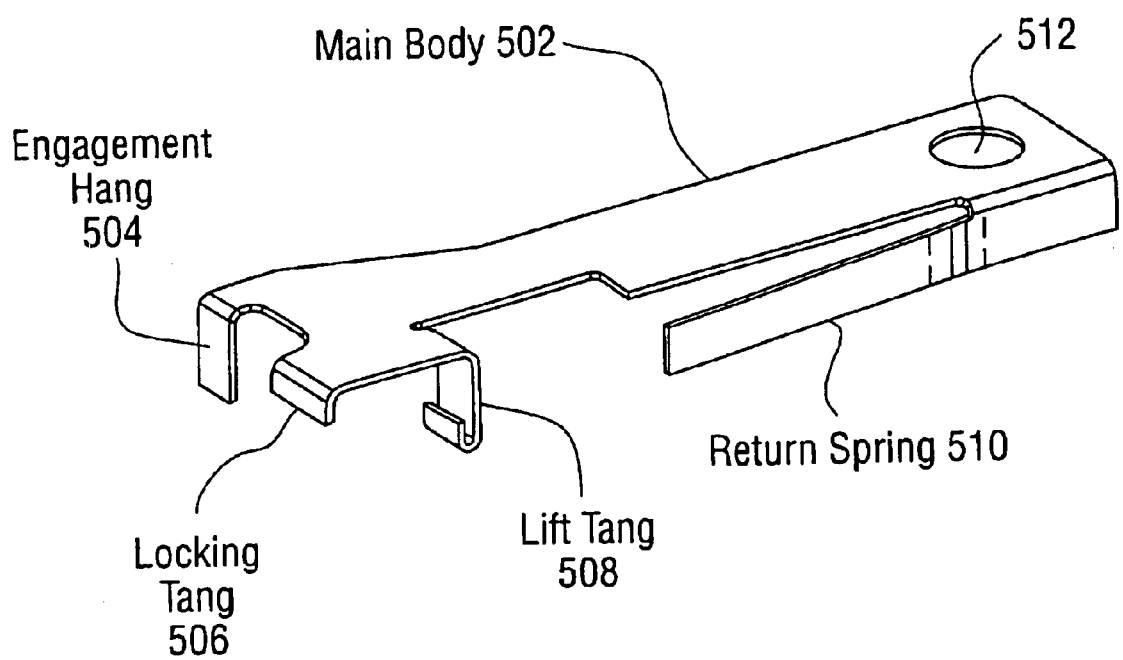
FIG. 5 illustrates in more detail the secondary lock of the preferred embodiment of the latching mechanism in accordance with the present invention.

FIG. 5 illustrates in more detail the secondary lock of the preferred embodiment of the latching mechanism in accordance with the present invention. The secondary lock 314 comprises a main body 502. At one end of the main body 502 and at the side nearer to the tray is an engagement tang 504. At same end of the main body 502 and at the side farther from the tray is a locking tang 506. In the preferred embodiment, the engagement 504 and locking 506 tangs protrude approximately perpendicular to the surface of the main body 502, with the locking tang 506 being shorter than the engagement tang 504. Between the engagement tang 504 and the locking tang 506 is a space in which the head 316 of the primary lock 302 may reside. Near the same end of the main body 502 and at the same side and behind the locking tang 506 is a lift tang 508. The lift tang 508 is positioned on the main body 502 such that it may reside within the notch 320 on the lock 302. At the other end of the main body 502 at the same side as the lift tang 508, there is a return spring 510. The return spring 510 is positioned such that when it is uncompressed, the main body 502 is pivoted clockwise. At the end opposite to the engagement tang 504 is a hole 512 in the main body 502 through which the retainer shift 306 resides. In the preferred embodiment, the secondary lock 314 is composed of beryllium copper, but other materials may be used.

The functioning of the primary 302 and secondary 314 locks in the latching of an accessory tray is described below in conjunction with FIGS. 6 through 12.

Figure 6:
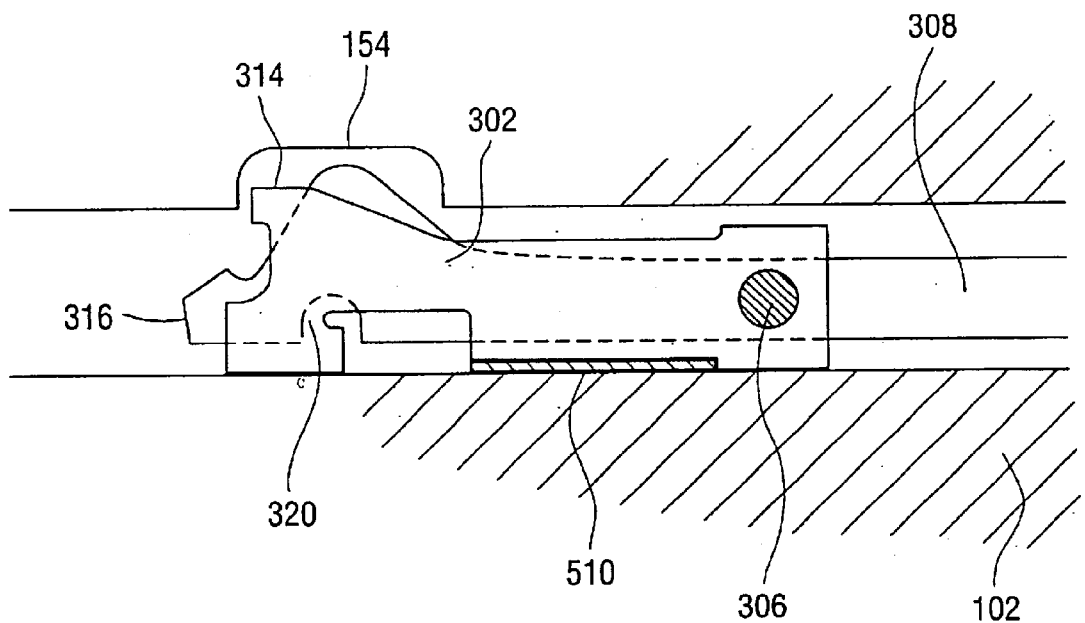
FIGS. 6 and 7 illustrate a top view and a side view, respectively, of the primary and secondary locks of the preferred embodiment of the latching mechanism in an unlocked position, before the accessory tray is inserted into the accessory holder, in accordance with the present invention.
Figure 7:
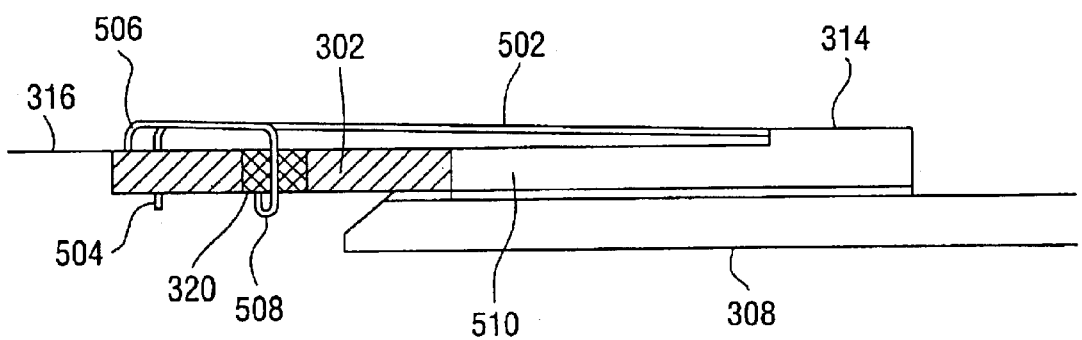

FIGS. 6 and 7 illustrate a top view and a side view, respectively, of the primary 302 and secondary 314 locks of the preferred embodiment of the latching mechanism in an unlocked position, before the accessory tray is inserted into the accessory holder, in accordance with the present invention. In FIG. 6, the retainer assembly 304 is not shown, and in FIG. 7, the frame 102 of the accessory holder 100 is not shown, so as to more clearly illustrate the functioning of the locks 302 and 314.

As illustrated in FIG. 6, the secondary lock 314 resides on top of the primary lock 302. Both the primary 302 and secondary 314 reside within the frame 102. In the unlocked, before tray insertion position, the return spring 510 is uncompressed, so that the side of the main body 502 with the locking 506 and lift 508 tangs are not abutted against the wall of the frame 102. Because of the opening 154 in the frame 102, the secondary lock 314 is free to be in this position. The primary lock 302 is in the position it would be in if the tray was inserted. As illustrated in FIG. 7, one end of the main body 502 is flexed such that the locking tang 506 rests on the top surface of the head 316 of the primary lock 302. The lift tang 508 resides within the notch 320 of the primary lock 302 so as not to interfere with the primary lock 302. The release assembly 308 resides underneath the primary 302 and secondary 314 locks in a position where it does not engage the lift tang 508. This is the default position of the primary 302 and secondary 314 locks.

Figure 8:
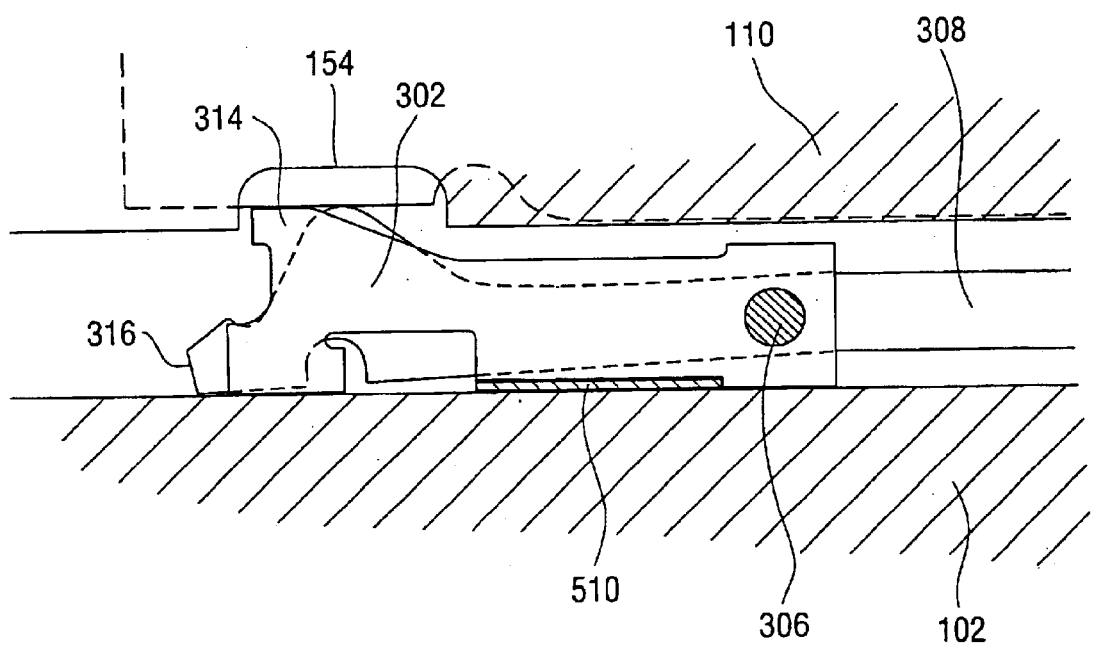
FIG. 8 illustrates a top view of the position of the primary and secondary locks of the preferred embodiment of the latching mechanism, as the accessory tray is being inserted, in accordance with the present invention.

FIG. 8 illustrates a top view of the position of the primary 302 and secondary 314 locks of the preferred embodiment of the latching mechanism, as the accessory tray is being inserted, in accordance with the present invention. The side of the tray 110 pushes upon the primary lock 302 and the engagement tang 504 of the secondary lock 314, causing them to pivot counterclockwise.

Figure 9:
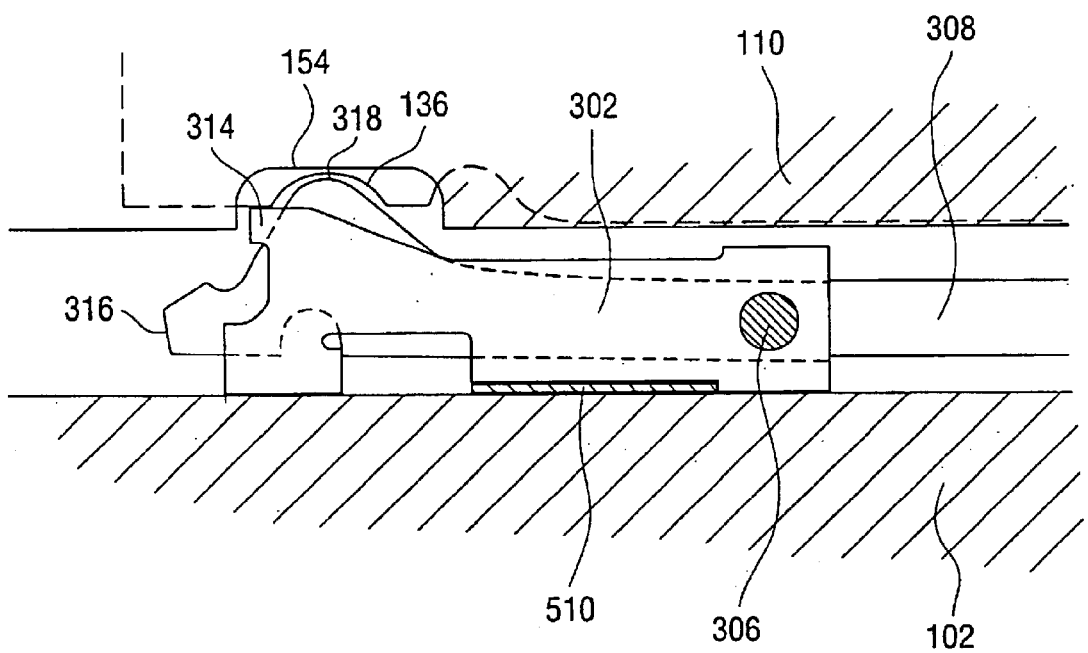
FIGS. 9 and 10 illustrate a top view and a side view, respectively, of the engaged position of the primary and secondary locks of the preferred embodiment of the latching mechanism in accordance with the present invention.
Figure 10:
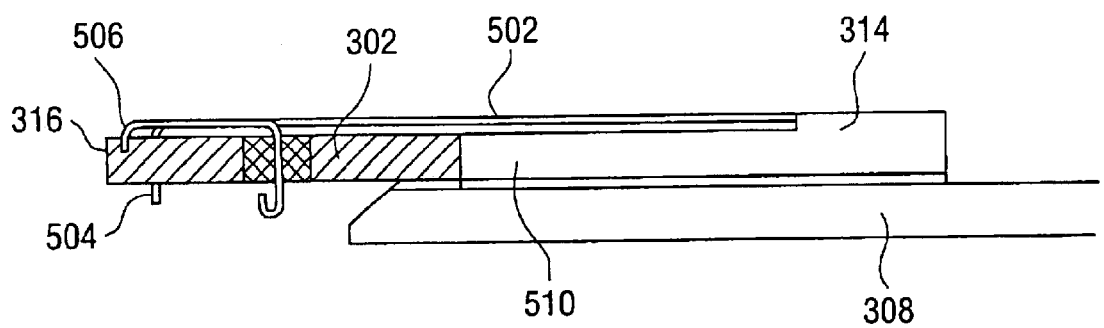

FIGS. 9 and 10 illustrate a top view and a side view, respectively, of the engaged position of the primary 302 and secondary 314 locks of the preferred embodiment of the latching mechanism in accordance with the present invention. As illustrated in FIG. 9, as the tray 110 is fully inserted, the protrusion 318 of the primary lock 302 springs clockwise, engaging the notch 136 of the tray 110. The secondary lock 314 remains in its counterclockwise pivoted position due to the side of the tray 110 pushing against the engagement tang 504. As the protrusion 318 engages the notch 136, the primary lock 302 clears the locking tang 506 of the secondary lock 314, allowing the main body 502 to unflex, as illustrated in FIG. 10. This results in the head 316 of the primary lock 302 being in the space between the engagement 504 and locking 506 tangs. The unflexing of the main body 502 in this manner places the locking tang 506 in the path of the primary lock 302, preventing the primary lock 302 from pivoting counterclockwise if a failure occurs elsewhere in the latching mechanism 300.

Figure 11:
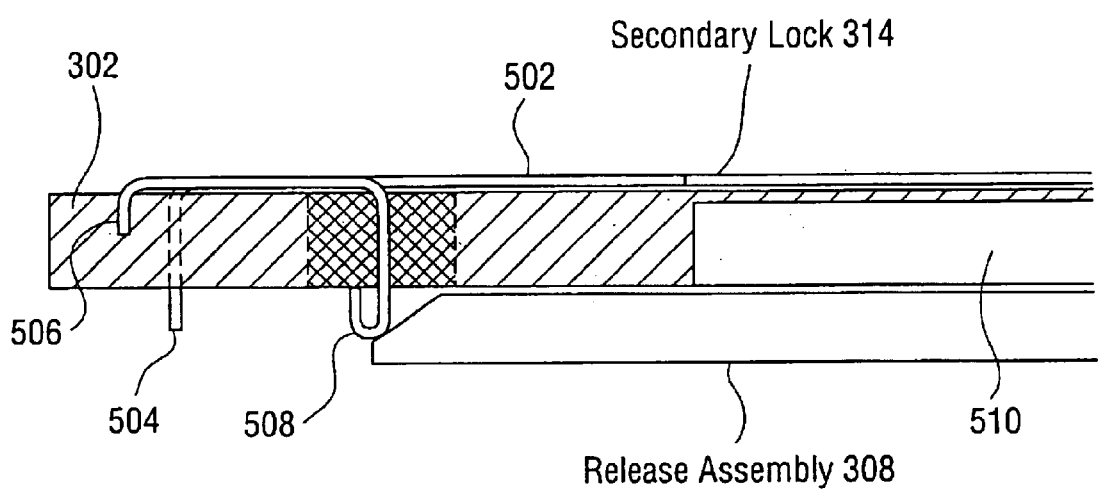
FIGS. 11 and 12 illustrates side views of the primary and secondary locks of the preferred embodiment of the latching mechanism, as they are disengaged by the pressing of the release button, in accordance with the present invention.
Figure 12:
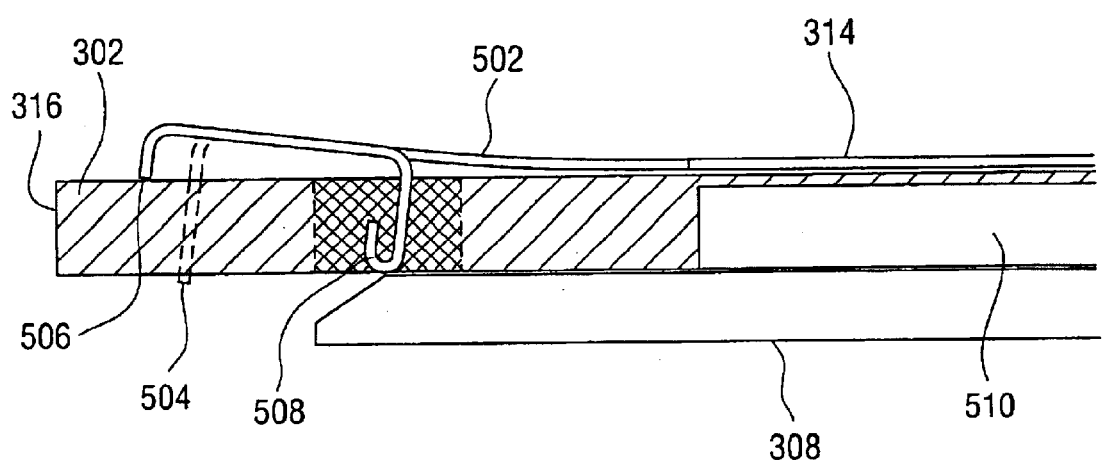

FIGS. 11 and 12 illustrate side views of the primary 302 and secondary 314 locks of the preferred embodiment of the latching mechanism, as they are disengaged by the pressing of the release button, in accordance with the present invention. As illustrated in FIG. 11, pressing the release button 312 compresses the button spring 310, pushes upon one end of the release assembly 308, moving it forward. The release assembly 308 has a wedge feature at the other end, which engages and pushes against the lift tang 508 of the secondary lock 314. As illustrated in FIG. 12, the angle of the wedge feature is such that the push of the lift tang 508 causes the main body 502 to flex upward until the locking tang 506 clears the primary lock 302. This removes the locking tang 506 from the path of the primary lock 302. Further pushing of the release button 312 also eventually causes a wedging action between an elongated hole (not shown) of the release assembly 308 and the self-clinching type pin (also not shown), in turn causing the primary lock 302 to pivot counterclockwise. This wedging action is analogous to the wedging action between the release assembly 126 and the roll pin 124 of the conventional latching mechanism 112. The wedging action does not occur upon the initial pushing of the release button 312. This delay is designed so that the primary lock 302 does not pivot until after the locking tang clears. Since the locking tang 506 is out from the primary lock's 302 path, the primary lock 302 is free to pivot counterclockwise until it disengages from the tray 110. The tray 110 may then be removed.

When the tray 110 is removed, it no longer holds the secondary lock in the engaged position, and the secondary lock 314 pivots clockwise due to the decompression of the return spring 510. As the release button 312 is released, the button spring 310 is uncompressed, moving the release assembly 308 backward away from the lift tang 508. This causes the locking tang 506 to rest upon the top surface of the head 316 of the primary lock 302, returning both the primary 302 and secondary 314 locks to their default positions, as illustrated in FIGS. 6 and 7.

In the above manner, a latching mechanism with a secondary lock is provided. The secondary lock prevents the primary lock from disengaging the tray even if another component in the mechanism fails, increasing the safety of the radiation therapy system significantly. Another important feature of the latching mechanism in accordance with the present invention is that the secondary lock remains in the default, disengaged position when no tray in inserted. This feature allows trays to be inserted without the need to press the release button first to set the secondary lock into the disengaged position.

Figure 13:
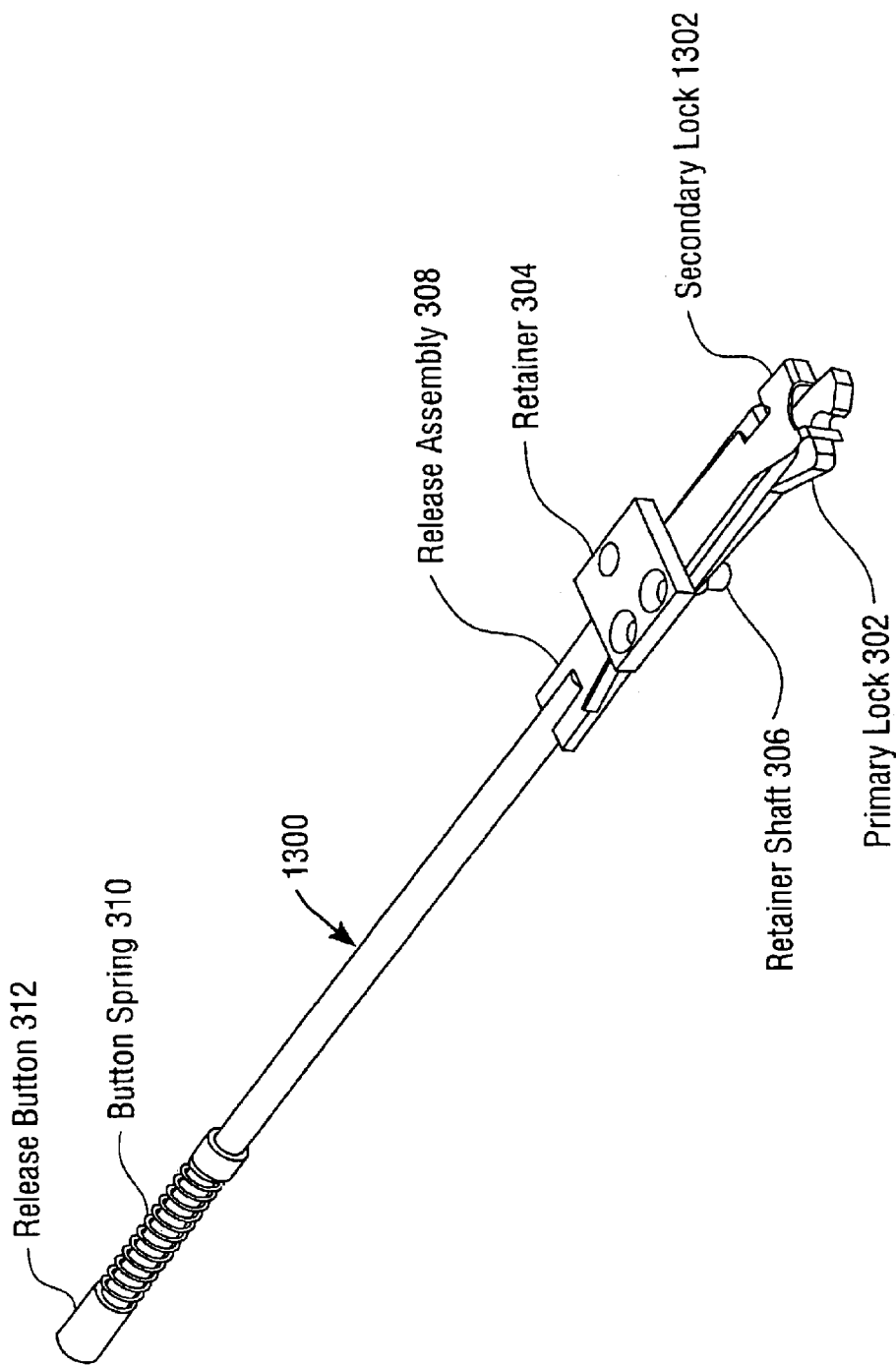
FIGS. 13 and 14 illustrate an alternative embodiment of a latching mechanism with a secondary lock in accordance with the present invention.
Figure 14:
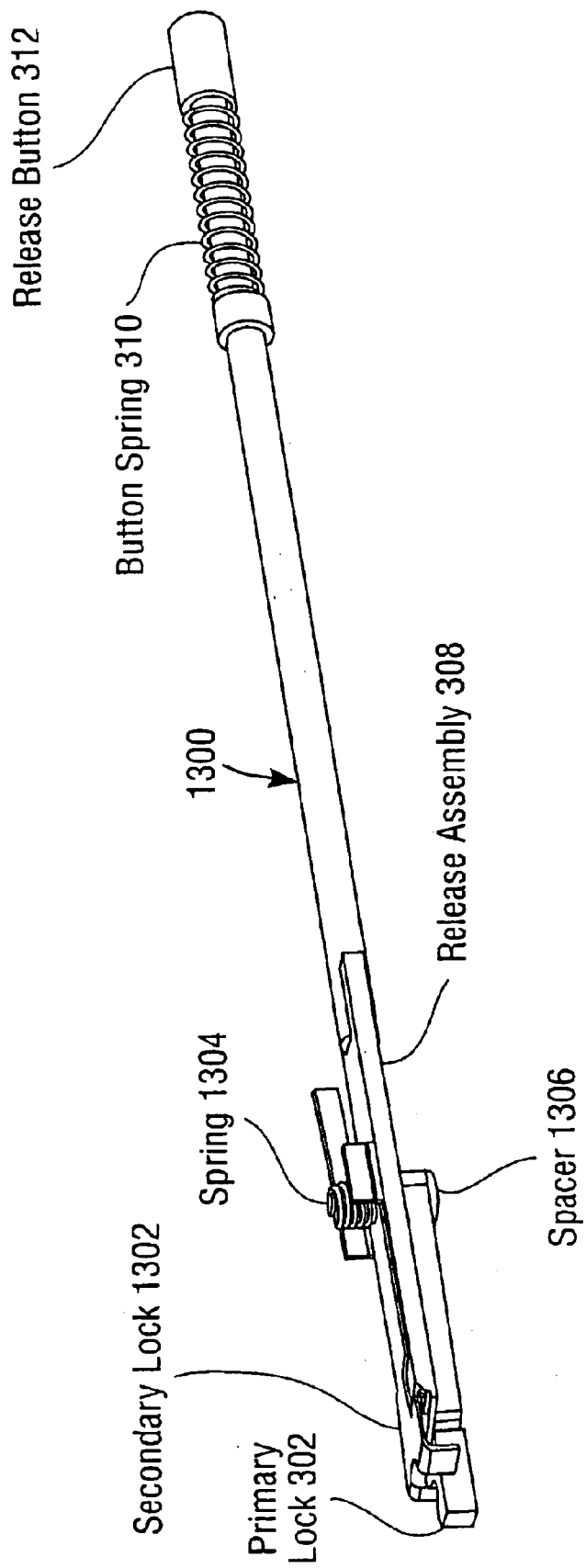

FIGS. 13 and 14 illustrate an alternative embodiment of a latching mechanism with a secondary lock in accordance with the present invention. FIGS. 13 and 14 illustrate the latching mechanisms 1300 from two different angles. The latching mechanism 1300 would latch an assembly tray in slot 108 of the assembly holder 100 (FIG. 2B). The latching mechanism 1300 have the same structure as the latching mechanisms 300 and 350 (FIGS. 3 and 4), except for an alternative configuration of the secondary lock. The spring 1304 and the spacer 1306 perform the same functions as the spring 324 and the spacers 322 of the preferred embodiment illustrated in FIG. 4.

Figure 15:
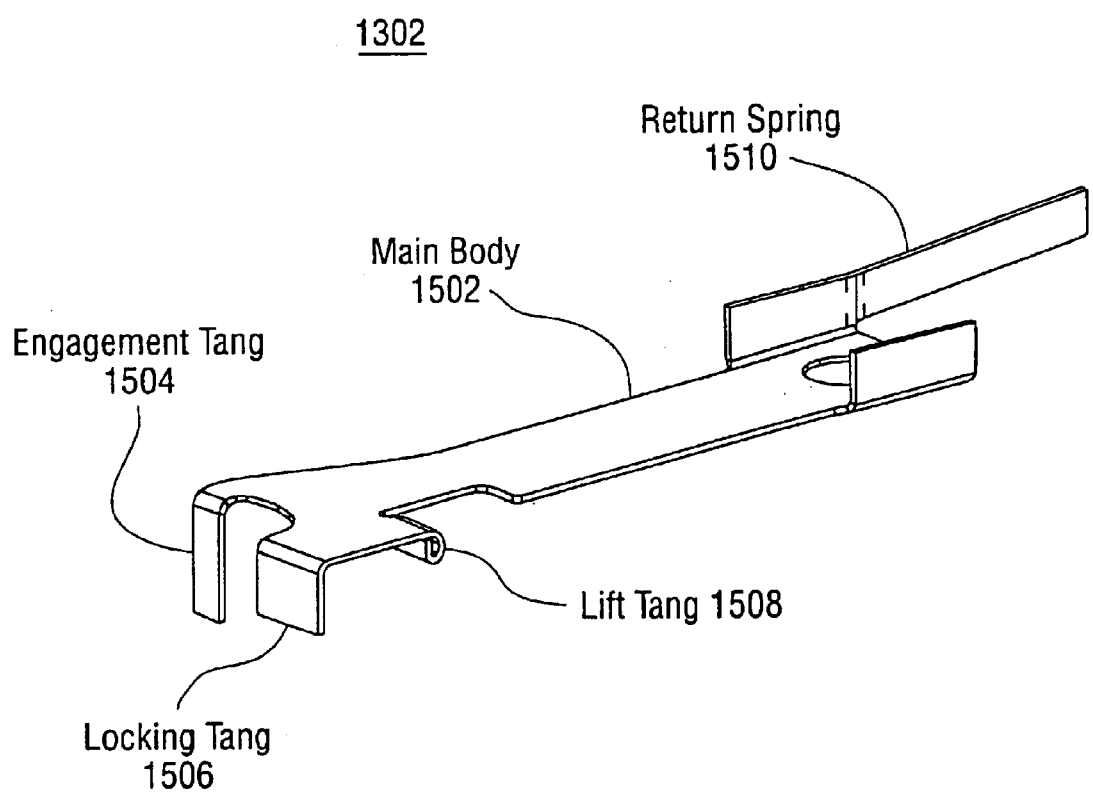
FIG. 15 illustrates in more detail the secondary lock of the alternative embodiment of the latching mechanism in accordance with the present invention.

FIG. 15 illustrates in more detail the secondary lock 1302 of the alternative embodiment of the latching mechanism in accordance with the present invention. The secondary lock 1302 comprises a main body 1502, an engagement tang 1504, a locking tang 1506, a lift tang 1508, and a return spring 1510. These elements of the secondary lock 1302 function under the same principles as the corresponding elements of the preferred embodiment of the secondary lock 314. The latching mechanism 1300 thus functions in the same manner as the latching mechanism 300. To avoid unnecessary repetition, the functioning of the latching mechanism 1300 will not be discussed further.

A system and method for a secondary lock for securing accessories in a radiation therapy system has been disclosed. The secondary lock provided in accordance with the present invention creates latching mechanism in a fail-safe locking system where the conditions are safe even if normal operation is lost. This fail-safe system is provided by the secondary lock which causes the primary lock to continue to engage an accessory tray even if failure occurs elsewhere in the latching mechanism. This lowers the probability of failure of the latching mechanism significantly, resulting in a safer radiation therapy system. The secondary lock of the latching mechanism in accordance with the present invention also remains in a disengaged position when no tray in inserted, allowing trays to be inserted without the need to press the release button first to set the secondary lock into the disengaged position.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A latching mechanism for latching an accessory to a frame of a radiation therapy system, comprising:
    a primary lock, comprising:
        a main body,
        an engagement tang at a first end and a first side of the main body,
        a locking tang at the first end and a second side of the main body, the second side of the main body being opposite to the first side of the main body, and
        a return spring at the second side of the main body wherein the main body is pivoted clockwise when the return spring is uncompressed; and
    a retainer shaft coupled to a second end of the primary lock and a second end of the main body, the second end of the primary lock being opposite to the first end of the primary lock, the second end of the main body being opposite to the first end of the main body, wherein the secondary lock is fixedly positioned when the protrusion engages the accessory and the head resides between the engagement tang and the locking tang.

2. The latching mechanism of claim 1, wherein the primary lock further comprises a notch at a second side of the primary lock, the second side being opposite to the first side of the primary lock.

3. A latching mechanism for latching an accessory to a frame of a radiation therapy system, comprising:
   a primary lock, comprising:
      a head at a first end of the primary lock, and
      a protrusion at a first side of the primary lock capable of engaging the accessory;
   a secondary lock, comprising:
      a main body,
      an engagement tang at a first end and a first side of the main body,
      a locking tang at the first end and a second side of the main body, the second side of the main body being opposite to the first side of the main body,
      a return spring at the second side of the main body, wherein the main body is pivoted clockwise when the return spring is uncompressed; and
      a lift tang at the second side of the main body, wherein the lift tang resides within a notch at a second side of the primary lock when the protrusion is not engaging the accessory, the second side of the primary lock being opposite to the first side of the primary lock;
   a retainer shaft coupled to a second end of the primary lock and a second end of the main body, the second end of the primary lock being opposite to the first end of the primary lock, the second end of the main body being opposite to the first end of the main body, wherein the secondary lock is fixedly positioned when the protrusion engages the accessory and the head resides between the engagement tang and the locking tang.

4. A latching mechanism for latching in accessory to a frame of a radiation therapy system, comprising:
   a primary lock, comprising:
      a head at a first end of the primary lock, and
      a protrusion at a first side of the primary lock capable of engaging the accessory;
   a secondary lock, comprising:
      a main body,
      an engagement tang at a first end and a first side of the main body, and
      a locking tang at the first end and a second side of the main body, the second side of the main body being opposite to the first side of the main body; and
   a retainer shaft coupled to a second end of the primary lock and a second end of the main body, the second end of the primary lock being opposite to the first end of the primary lock, the second end of the main body being opposite to the first end of the main body, wherein the secondary lock is fixedly positioned when the protrusion engages the accessory and the head resides between the engagement tang and the locking tang;
   release assembly comprising a first end with a wedge feature, a second end opposite to the first end, and an elongated hole, wherein the retainer shaft resides within the elongated hole;
   a self-clinching type pin coupled to the release assembly and the primary lock;
   a release button spring coupled to the release assembly;
   a release button coupled to the second end of the release assembly and the release button spring, wherein when the release button is pressed, the release button spring is compressed, the wedge feature of the release assembly engages a lift tang of the secondary lock, and the self-clinching type pin pivots the primary lock away from the accessory.

5. A latching mechanism for latching an accessory to a frame of a radiation therapy system, comprising:
   a primary lock, comprising:
      a head at a first end of the primary lock,
      a protrusion at a first side of the primary lock capable of engaging the accessory, and
      a notch at a second side of the primary lock, the second side being opposite to the first side;
   a secondary lock, comprising:
      a main body,
      an engagement tang at a first end and a first side of the main body, and
      a locking tang at the first end and a second side of the main body, the second side of the main body being opposite to the first side of the main body,
      a return spring at the second side of the main body, wherein the main body is pivoted clockwise when the return spring is uncompressed, and
      a lift tang at the second side of the main body, wherein the lift tang resides within the notch when the protrusion is not engaging the accessory; and
   a retainer shaft coupled to a second end of the primary lock and a second end of the main body, the second end of the primary lock being opposite to the first end of the primary lock, the second end of the main body being opposite to the first end of the main body, wherein the primary and secondary locks are capable of pivoting around an axis of the retainer shaft, wherein the secondary lock is fixedly positioned when the protrusion engages the accessory and the head resides between the engagement tang and the locking tang.

6. The latching mechanism of claim 5, further comprising:
   a release assembly comprising a first end with a wedge feature, a second end opposite to the first end, and an elongated hole, wherein the retainer shaft resides within the elongated hole;
   a self-clinching type pin coupled to the release assembly and the primary lock;
   a release button spring coupled to the release assembly;
   a release button coupled to the second end of the release assembly and the release button spring, wherein when the release button is pressed, the release button spring is compressed, the wedge feature of the release assembly engages the lift tang, and the self-clinching type pin pivots the primary lock away from the accessory.

7. A latching mechanism for latching an accessory to a frame of a radiation therapy system, comprising:
   a primary lock, comprising:
      a head at a first end of the primary lock,
      a protrusion at a first side of the primary lock capable of engaging the accessory, and
      a notch at a second side of the primary lock, the second side being opposite to the first side;
   a secondary lock, comprising:
      a main body,
      an engagement tang at a first end and a first side of the main body, and
      a locking tang at the first end and a second side of the main body, the second side of the main body being opposite to the first side of the main body,
      a return spring at the second side of the main body, wherein the main body is pivoted clockwise when the return spring is uncompressed, and a lift tang at the second side of the main body, wherein the lift tang resides within the notch when the protrusion is not engaging the accessory;

a retainer shaft coupled to a second end of the primary lock and a second end of the main body, the second end of the primary lock being opposite to the first end of the primary lock, the second end of the main body being opposite to the first end of the main body, wherein the primary and secondary locks are capable of pivoting around an axis of the retainer shaft, wherein the secondary lock is fixedly positioned when the protrusion engages the accessory and the head resides between the engagement tang and the locking tang;

a release assembly, comprising a first end with a wedge feature, a second end opposite to the first end, and an elongated hole, wherein the retainer shaft resides within the elongated hole;

a self-clinching type pin coupled to the release assembly and the primary lock;

a release button spring coupled to the release assembly; and a release button coupled to the second end of the release assembly and the release button spring, wherein when the release button is pressed, the release button spring is compressed, the wedge feature of the release assembly engages the lift tang, and the self-clinching type pin pivots the primary lock away from the accessory.

8. A latching mechanism for latching an accessory to a frame of a radiation therapy system, comprising:

a primary lock, comprising:
  a head at a first end of the primary lock, and
  a protrusion at a first side of the primary lock capable of engaging the accessory;

a secondary lock, comprising:
  a main body,
  an engagement tang at a first end and a first side of the main body,
  a locking tang at the first end and a second side of the main body, the second side of the main body being opposite to the first side of the main body, and
  a lift tang at the second side of the main body, wherein the lift tang resides within a notch at a second side of the primary lock when the protrusion is not engaging the accessory, the second side of the primary lock being opposite to the first side of the primary lock; and a retainer shaft coupled to a second end of the primary lock and a second end of the main body, the second end of the primary lock being opposite to the first end of the primary lock, the second end of the main body being opposite to the first end of the main body, wherein the secondary lock is fixedly positioned when the protrusion engages the accessory and the head resides between the engagement tang and the locking tang.

* * * * *